(12) United States Patent
Hazen et al.

(10) Patent No.: US 8,216,976 B2
(45) Date of Patent: *Jul. 10, 2012

(54) HERBICIDAL COMPOSITIONS

(75) Inventors: James Lyle Hazen, Young Harris, GA (US); Aleksander Edward Karczewski, Oakland, CA (US); Yabin Lei, Holmdel, NJ (US); Jane Qing Liu, Pleasanton, CA (US); Evelyn Jean Taylor, San Ramon, CA (US)

(73) Assignees: Valent U.S.A. Corporation, Walnut Creek, CA (US); Akzo Nobel Surface Chemistry, L.L.C., Chicago, IL (US)

( * ) Notice: Subject to any disclaimer, the term of this patent is extended or adjusted under 35 U.S.C. 154(b) by 160 days.

This patent is subject to a terminal disclaimer.

(21) Appl. No.: 12/634,033

(22) Filed: Dec. 9, 2009

(65) Prior Publication Data

US 2010/0087318 A1 Apr. 8, 2010

Related U.S. Application Data

(63) Continuation of application No. 10/974,711, filed on Oct. 28, 2004, now Pat. No. 7,651,977.

(51) Int. Cl.
*A01N 47/28* (2006.01)
*A01N 47/40* (2006.01)
(52) U.S. Cl. ........................................ 504/148; 504/141
(58) Field of Classification Search ................. 504/148, 504/141
See application file for complete search history.

(56) References Cited

U.S. PATENT DOCUMENTS

| | | | |
|---|---|---|---|
| 7,651,977 B2 * | 1/2010 | Hazen et al. | 504/141 |
| 2004/0018940 A1 | 1/2004 | Hacker et al. | |

* cited by examiner

*Primary Examiner* — Shengjun Wang
(74) *Attorney, Agent, or Firm* — Wood, Phillips, Katz, Clark & Mortimer

(57) ABSTRACT

The present invention provides an improved herbicidal composition including (a) an effective amount of an herbicidal cyclohexandione oxime compound or agriculturally acceptable salt thereof; (b) one or more esters of a fatty acid; (c) a salt of dodecylbenzensulfonic acid; (d) at least one nonionic surfactant selected from the group consisting of polyoxyethylene plant oils and polyoxyethylene sorbitan esters; and (e) optionally another herbicide.

19 Claims, No Drawings

HERBICIDAL COMPOSITIONS

This application is a continuation of U.S. patent application Ser. No. 10/974,711, filed on Oct. 28, 2004.

FIELD OF THE INVENTION

The present invention relates to herbicidal compositions. More particularly, the present invention relates to improved adjuvant-containing formulations suitable as postemergent herbicides which improve the efficacy of herbicides.

BACKGROUND OF THE INVENTION

It is known that herbicidal compositions containing cyclohexanedione oxime compounds such as clethodim, sethoxydim, alloxydim, cycloxydim, butroxydim, tralkoxydim, tepraloxydim, and profoxydim are difficult to formulate, since the active ingredients are sensitive to chemical instability. Many adjuvant materials, surfactants, and even water, for example, can lead to significant chemical degradation. Because chemical stability is commercially desirable, as well as required by the Environmental Protection Agency, it is common in the agricultural chemical industry to formulate cyclohexanedione oxime compounds with an emphasis on chemical stability and good mixing characteristics, rather than on optimization of herbicidal efficacy.

Current graminicides typically require the addition of oil-based adjuvants (known as "crop oil concentrates") in order to achieve commercially acceptable stability and weed control. In particular, herbicidal efficacy for cyclohexanedione oxime compounds requires adding crop oil concentrates at the time of application in the grower fields. Rather than having to prepare a tank mix from separate herbicide and crop oil containers, it would be commercially desirable to prepare herbicides and crop oils in one formulation which is ready to dilute. However, because crop oil concentrates commonly used in the marketplace are recommended at the use rate of 16 to 32 fluid ounces per acre, it has not been practical to provide cyclohexanedione oxime compounds and crop oil concentrates as premixed, ready to dilute formulations.

Ready to dilute adjuvant-containing post-emergent herbicidal formulations are described in U.S. Pat. No. 5,084,087. The formulation comprises a mixture of one or more herbicidal compounds, a polyoxyalkylene nonionic surfactant having a hydrophilic-lipophilic balance (HLB) of from 10 to about 14, an anionic surfactant selected from the group consisting of the dialkyl metal sulfosuccinates and the metal alkylbenzene sulfonates, optionally a low foaming polyoxyalkylene nonionic surfactant having an HLB of less than 10, and a lower alkanol ester of a long chain fatty acid. This patent does not describe or suggest the particular herbicidal composition of the present invention, including the surfactant component and advantageous properties described herein.

SUMMARY OF THE INVENTION

An object of the present invention is to provide improved herbicidal compositions and methods of use which exhibit excellent herbicidal efficacy and chemical stability. These and other objects and advantages of the present invention have been achieved by providing an herbicidal composition comprising (a) an effective amount of an herbicidal cyclohexanedione oxime compound or agriculturally acceptable salt thereof; (b) one or more esters of a fatty acid; (c) a salt of dodecylbenzenesulfonic acid; and (d) at least one nonionic surfactant selected from the group consisting of polyoxyethylene plant oils and polyoxyethylene sorbitan esters. As an additional, optional, component, an aromatic hydrocarbon solvent may be used.

In a preferred embodiment, the present invention provides an herbicidal composition comprising (a) about 1 to 40% by weight of the herbicidal cyclohexanedione oxime compound or agriculturally acceptable salt thereof; (b) about 10 to 90% by weight of the one or more esters of a fatty acid; (c) about 0.1 to 5% by weight of the salt of dodecylbenzenesulfonic acid; and (d) about 0.2 to 12% by weight of the at least one nonionic surfactant mentioned above.

In a second preferred embodiment, the present invention provides an herbicidal composition comprising (a) about 1 to 40% by weight of the herbicidal cyclohexanedione oxime compound or agriculturally acceptable salt thereof; (b) about 10 to 75% by weight of the one or more esters of a fatty acid; (c) about 0.1 to 5% by weight of the salt of dodecylbenzenesulfonic acid; (d) about 0.2 to 12% by weight of the at least one nonionic surfactant mentioned above; and (e) about 10 to 90% by weight of the aromatic hydrocarbon solvent.

In a more preferred embodiment, the present invention provides an herbicidal composition comprising (a) 10 to 30% by weight of clethodim; (b) 20 to 50% by weight of a mixture of the methyl esters of C16-C18 fatty acids; (c) 1 to 5% by weight of polyoxyethylene castor oil and/or polyoxyethylene sorbitan monotallate; (d) 0.5 to 3% by weight of calcium dodecylbenzenesulfonate; and (e) 10 to 60% by weight of the aromatic hydrocarbon solvent.

In a further embodiment, the present invention provides a method for controlling the growth of vegetation, comprising applying to the vegetation an effective amount of the herbicidal composition described above.

DETAILED DESCRIPTION OF THE INVENTION

The herbicidal compositions of the present invention offer several advantages, including, for example, one or more of the following: they are chemically stable formulations, they do not require the addition of a crop oil concentrate, they provide superior control of susceptible weed species, provide increased speed of herbicide absorption and herbicide symptoms, they result in increased speed of glyphosate absorption, and they can be tank mixed with other herbicides without a decrease in weed control.

The herbicidal ingredient of the present invention is an herbicidal compound having a cyclohexanedione oxime structure. Certain cyclohexanedione oximes are known in the art as having excellent herbicidal activity against a variety of post-emergent grasses in a variety of environments. Typical examples include clethodim, sethoxydim, alloxydim, cycloxydim, butroxydim, tralkoxydim, tepraloxydim, and profoxydim. Cyclohexanedione oximes can be obtained on the market. For example, clethodim is provided by Valent U.S.A. Corporation or Arvesta Corporation, sethoxydim and alloxydim are provided by Nippon Soda Company or BASF Corporation, cycloxydim and profoxydim are provided by BASF Corporation, and butroxydim is provided by CropCare Australasia. Alloxydim is usually provided as its sodium salt. Preferred cyclohexanedione oximes are clethodim and sethoxydim. Most preferred is clethodim. The active ingredient can be employed in several technical forms such as Clethodim Technical (Valent U.S.A. Corporation or Arvesta Corporation), which comprises 95.3% clethodim by weight and 4.7% inert ingredients, and a 70% or 37% Manufacturing Use Product which is a solution of Clethodim Technical in aromatic solvent. For any of the cyclohexanedione oxime compounds which have an optically active center, such as clethodim, both racemic and enantiomeric forms may be used as desired.

The content of the herbicidal cyclohexanedione oxime compound in the herbicidal composition is preferably about 1% to 40% by weight, more preferably 3% to 30% by weight, and most preferably 10% to 30% by weight.

The esters of a fatty acid are preferably C1-C8 alkyl (e.g. methyl, ethyl, isopropyl, butyl, isobutyl, octyl) esters of a fatty acid. The fatty acids can be saturated or unsaturated organic monobasic acids such as palmitic acid, myristic acid, stearic acid, lauric acid or oleic acid. The carbon numbers of the fatty acids are preferably 12 to 22. Typical non-limiting examples include methyl oleate, methyl palmitate, isopropyl myristate, octyllaurate, isopropyl palmitate, and butyl stearate. The preferred esters of a fatty acid are a mixture comprised predominantly of the methyl esters of C16-C18 fatty acids.

The C16-C18 fatty acid methyl ester mixture used in the herbicidal formulations tested in the examples set forth herein was CE-1618 (C16 23-32%, C18 65-75%, primarily methyl oleate), available from Proctor and Gamble. Other suitable esters of fatty acids include but are not limited to CE-1695, CE-1897, SE-1885, also available from Proctor and Gamble; AGNIQUE® ME and AE products, available from Cognis Corporation; STEPAN C-65 and C-68 and KESSCO® IPP, IPM and BS, available from Stepan Company; and PRIOLUBE® 1530 and 1400, available from Uniqema.

The content of the esters of a fatty acid in the herbicidal composition is preferably about 10% to 90% by weight, more preferably 20% to 70% by weight, most preferably 20% to 50% by weight.

The ratio of the esters of a fatty acid to the herbicidal ingredient is preferably 0.5:1 to 25:1, more preferably 0.8:1 to 12:1, and most preferably 1:1 to 4:1.

The salt of dodecylbenzenesulfonic (DDBS) acid is preferably a salt that can work as an anionic surfactant, and typically is a calcium, sodium, potassium, or amine salt. The preferred salt is calcium DDBS.

[18] The calcium DDBS used in the herbicidal formulations tested in the Examples set forth herein was WITCONATE® P-1220EH (60% CaDDBS, 15% propylene glycol, and 25% 2-ethylhexanol), available from Akzo Nobel. Other suitable salts of DDBS include but are not limited to WITCONATE® P 1860, P 5020 B, P 1020 B, and P 1060 B, also available from Akzo Nobel; AGNIQUE® ABS products, available from Cognis Corporation; NINATE® 401-A, available from Stepan Company; and RHODACAL® 60BE, 60BHF and 70B, available from Rhodia.

The content of the salt of DDBS acid in the herbicidal composition is preferably about 0.1% to 5% by weight, more preferably 0.5% to 5% by weight, and most preferably 0.5% to 3% by weight.

The nonionic surfactant is selected from the group consisting of polyoxyethylene (POE) plant oils and POE sorbitari esters. The POE plant oils may be hydrogenated. Examples of the plant oils include but are not limited to castor oil, rapeseed oil and linseed oil. The HLB of the polyoxyethylene plant oil is preferably 14.4-18.0. A preferred POE plant oil is POE (54 moles ethylene oxide (EO)) castor oil (POE (54) castor oil), which has an HLB of 14.4.

The POE (54) castor oil used in the herbicidal formulations tested in the Examples set forth herein was EMULPON® CO-550, available from Akzo Nobel. Other suitable polyoxyethylene plant oils include but are not limited to AGNIQUE® CSO, SBO and RSO products, available from Cognis Corporation; and ALKAMULS® OR-40 and EL-719, available from Rhodia.

The POE sorbitan esters of the present invention are preferably the ethoxylated sorbitan esters of fatty acids. The fatty acid may be derived from animal or vegetable sources. The definition of the fatty acid is as described above. Typical examples include but are not limited to POE sorbitan monotallate, POE sorbitan monooleate, POE sorbitan trioleate, POE sorbitan monostearate, POE sorbitan tristearate, POE sorbitan monomyristate, and POE sorbitan monolaurate. The HLB of the POE sorbitan ester is preferably 14.4-18.0. A preferred POE sorbitan ester is POE (30 moles EO) sorbitan monotallate (POE(30) sorbitan monotallate), which has a HLB of 15.4.

The POE (30) sorbitan monotallate used in the herbicidal formulations tested in the Examples set forth herein was ARMOTAN® AL 69-66, available from Akzo Nobel. Other suitable POE sorbitan esters include but are not limited to ARMOTAN® SMO 20, also available from Akzo Nobel; AGNIQUE® SML, SMS, STS, and SMO products, available from Cognis Corporation; TOXIMUL® SEE-340 and 341, available from Stepan Company, and ALTOX® 80 and 8916TF, TWEEN® 20, 40, and 60, available from Uniqema.

The content of the nonionic surfactant in the herbicidal composition is preferably about 0.2% to 12% by weight, more preferably 0.5% to 8% by weight, and most preferably 1% to 5% by weight.

The optional aromatic hydrocarbon solvent is not restricted so long as it can dissolve the herbicidal cyclohexanedione oxime compound. Aromatic hydrocarbon solvents are readily available from a number of sources. Examples include but are not limited to xylene; phenylxylylethane; HISOLO SAS-296 (a mixture of 1-phenyl-1-xylylethane and 1-phenyl-1-ethylphenylethane), available from Nippon Petroleum Company; CACTUS SOLVENT® HP-DMN (containing 80% of dimethylnaphthalene) and CACTUS SOLVENT® P-100 (alkylbenzene having carbon number of 9 to 10), available from Nikko Petrochemical Company; SOLVESSO™ 100 and AROMATIC 100, AROMATIC 150 and SOLVESSO™ 150, SOLVESSO™ 200 and AROMATIC 200 (aromatic hydrocarbons), available from ExxonMobil Chemical; and HI-SOL® 10 and HI-SOL® 15 (aromatic hydrocarbons), available from Ashland Chemical Company.

[26] Preferred aromatic hydrocarbon solvents are AROMATIC 150 and SOLVESSO™ 150, and HI-SOL® 15. AROMATIC 150 was used in the herbicidal formulations tested in the Examples set forth herein.

[27] The content of the aromatic hydrocarbon solvent in the herbicidal composition is preferably up to about 90% by weight, more preferably 10% to 75% by weight, and most preferably 10% to 60% by weight.

Further, the herbicidal composition optionally comprises another solvent, and/or auxiliary components such as antioxidant (e.g., propyl gallate, ascorbyi palmitate, butylated hydroxy toluene, or butylated hydroxyanisole), thickener, antifoaming agent, perfume and dyestuff.

Examples of other solvents include but are not limited to 2-ethylhexanol, propylene glycol, ethylene glycol, diethylene glycol, and glycerin. When 2-ethylhexanol or propylene glycol is used, the content of the additional solvent in the herbicidal composition is preferably about 0.5% to 4% by weight.

[30] In the herbicidal formulations tested in the Examples set forth herein, small amounts of 2-ethylhexanol and propylene glycol were carried over from the source of the salt of DDBS acid (WITCONATE® P-1220EH (60% CaDDBS, 15% propylene glycol, and 25% 2-ethylhexanol), available from Akzo Nobel).

When the antioxidant propyl gallate is used, the content of the propyl gallate in the herbicidal composition is preferably about 0.01% to 1% by weight, more preferably 0.05% to 0.5% by weight. Preferred embodiments of the herbicidal composition of the present invention include 0.25% propyl gallate by weight.

The herbicidal composition of the present invention can be prepared by mixing (a) an herbicidal cyclohexanedione oxime compound or agriculturally acceptable salt thereof as an herbicidal ingredient, (b) one or more esters of a fatty acid, (c) a salt of DDBS acid, (d) at least one nonionic surfactant selected from the group consisting of POE plant oils and POE sorbitan esters and (e) optionally an aromatic hydrocarbon solvent, and optionally other solvents, auxiliaries and so on. There are no specific mixing condition requirements, and the components do not need to be added in any particular order. However, when an antioxidant such as propyl gallate is used, it may be desirable to premix the antioxidant with the nonionic surfactant(s) or with a mixture of the nonionic surfactant(s), the salt of DDBS acid, and the one or more esters of a fatty acid.

The herbicidal compositions of the present invention are typically utilized as emulsifiable concentrates, namely they are diluted with water to give an emulsion and applied to weeds, especially graminaceous weeds such as barnyardgrass (*Echinochloa crus-galli*), green foxtail (*Setaria viridis*), giant foxtail (*Setaria fa beri*), large crabgrass (*Digitaria sanguinalis*), annual bluegrass (*Poa annua*), blackgrass (*Alopecurus myosuroides*), oats (*Avena sativa*), wild oats (*Avena fatua*), johnsongrass (*Sorghum halepense*), quackgrass (*Agropyron repens*), downy brome (*Bromus tectorum*), and bermudagrass (*Cynodon dactylon*), in broad-leaf crop (e.g. soybean, cotton, sugarbeet, peanut, alfalfa, potatoes, flax, canola, sunflowers, fruiting vegetables, legume crops, cranberries, cucurbit crops, head and stem *brassica* crops, leafy *brassica* crops, lettuce crops, mustard seed, onion, garlic, shallots, leaks, root vegetables, rhubarb, spinach, strawberry, sweet potato, and many other crops) fields.

The application dosage is generally about 0.063 to 0.250 pounds active ingredient per acre (about 70 to 280 grams of active ingredient per hectare) in the amount of the herbicidal cyclohexanedione oxime compound. One of ordinary skill in the art could determine an appropriate application dosage, which may vary with crop, objective weeds, weather conditions and so on. The dilution of the herbicidal composition can be used for aerial application by helicopter, plane or radio-controlled helicopter.

One of the advantages of the herbicidal composition of the present invention is its ability to achieve commercially acceptable weed control (>90%) without the need for tank mixing with crop oil concentrates, crop oil concentrate blends, nonionic surfactant adjuvants, or ammonium sulfate. However, in certain circumstances, these materials may be desirable to increase efficacy, or may be required by a tank-mix partner. For example, glyphosate formulations commonly require the addition of ammonium sulfate. Examples of crop oil concentrates, crop oil concentrate blends, or nonionic surfactant adjuvants that can be used with the present invention include AGRI-DEX®, DYNE-AMIC®, and INDUCE®, available from Helena Chemical Corporation; SILWET® L-77, available from Loveland Industries; PRIME OIL® and PRIME OIL® EV, DESTINY®, and PREFERENCE®, manufactured by Agriliance; HERBIMAX® and MSO® CONCENTRATE, manufactured by Loveland Industries; BRITZ O/S BLEND, manufactured by Britz Fertilizers, Incorporated; and MORACT®, manufactured by Wilbur-Ellis.

In addition, under practical conditions it can be desirable to mix herbicides to achieve a broader spectrum of weed control, for example to prevent the need to make two separate applications of individual herbicides, such as one to control grass weeds and a second to control broadleaf weeds. However, mixing herbicides can be problematic if there is antagonism between the active ingredients, between the formulations, or between the adjuvant recommendations. The present invention overcomes those limitations with respect to glyphosate formulations, and also with respect to other herbicides such as but not limited to CADRE® (active ingredient imazapic, available from BASF Corporation), STORM™ (active ingredients acifluorfen and bentazon, available from United Phosphorus, Incorporated), and COBRA® (active ingredient lactofen, available from Valent U.S.A. Corporation).

EXAMPLES

To illustrate the invention, specific examples are set forth below. These examples are merely illustrations and are not to be understood as limiting the scope and underlying principles of the invention in any way. Various modifications of the invention in addition to those shown and described herein will become apparent to those skilled in the art from the following examples and foregoing description. Such modifications are also intended to fall within the scope of the appended claims.

In the following examples, herbicidal formulations of the present invention are tested for their efficacy against a variety of common weeds. In many cases, comparisons are made to similar commercially available herbicidal formulations which contain clethodim as the active ingredient. One such commercially available herbicidal formulation used for comparison purposes is PRISM® 1 EC, a product of Valent U.S.A. Corporation. Another commercially available herbicidal formulation used for comparison purposes is SELECT® 2 EC, also a product of Valent U.S.A. Corporation.

In all the tables showing efficacy of the herbicidal formulations against various species of weeds, the numerical values represent the percentage of weed control, or percent kill of the various species. The use rate of the herbicidal formulations is expressed in terms of pounds of active ingredient per acre (lb ai/A).

Several herbicidal formulations of the present invention were tested in the following examples. These herbicidal formulations are defined as follows:

| Formulation A | |
|---|---|
| | % by weight |
| Clethodim Technical | 13.2 |
| C16-C18 fatty acid methyl esters | 35.3 |
| Ca DDBS | 1.5 |
| POE(54) castor oil | 1.2 |
| POE(30) sorbitan monotallate | 1.0 |
| Propyl gallate | 0.2 |
| 2-Ethylhexanol | 0.6 |
| Propylene glycol | 0.4 |
| AROMATIC 150 | balance |

Formulation B

| | % by weight |
|---|---|
| Clethodim Technical | 21.4 |
| C16-C18 fatty acid methyl esters | 26.5 |
| Ca DDBS | 1.1 |
| POE(54) castor oil | 0.9 |
| POE(30) sorbitan monotallate | 0.8 |
| Propyl gallate | 0.2 |
| 2-Ethylhexanol | 0.5 |
| Propylene glycol | 0.3 |
| AROMATIC 150 | balance |

Formulation C

| | % by weight |
|---|---|
| Clethodim Technical | 3.5 |
| C16-C18 fatty acid methyl esters | 70.6 |
| Ca DDBS | 3.0 |
| POE(54) castor oil | 2.3 |
| POE(30) sorbitan monotallate | 2.1 |
| Propyl gallate | 0.2 |
| 2-Ethylhexanol | 1.2 |
| Propylene glycol | 0.7 |
| AROMATIC 150 | balance |

Formulation D

| | % by weight |
|---|---|
| Clethodim Technical | 7.0 |
| C16-C18 fatty acid methyl esters | 70.6 |
| Ca DDBS | 3.0 |
| POE(54) castor oil | 2.3 |
| POE(30) sorbitan monotallate | 2.1 |
| Propyl gallate | 0.2 |
| 2-Ethylhexanol | 1.2 |
| Propylene glycol | 0.7 |
| AROMATIC 150 | balance |

Formulation E

| | % by weight |
|---|---|
| Clethodim Technical | 24.9 |
| C16-C18 fatty acid methyl esters | 22.1 |
| Ca DDBS | 0.9 |
| POE(54) castor oil | 0.7 |
| POE(30) sorbitan monotallate | 0.6 |
| Propyl gallate | 0.2 |
| 2-Ethylhexanol | 0.4 |
| Propylene glycol | 0.2 |
| AROMATIC 150 | balance |

Formulation F

| | % by weight |
|---|---|
| Clethodim Technical | 14.1 |
| C16-C18 fatty acid methyl esters | 35.4 |
| Ca DDBS | 1.5 |

Formulation F -continued

| | % by weight |
|---|---|
| POE(54) castor oil | 1.2 |
| POE(30) sorbitan monotallate | 1.0 |
| Propyl gallate | 0.3 |
| 2-Ethylhexanol | 0.6 |
| Propylene glycol | 0.4 |
| AROMATIC 150 | balance |

Formulation G

| | % by weight |
|---|---|
| Clethodim Technical | 25.5 |
| C16-C18 fatty acid methyl esters | 24.9 |
| Ca DDBS | 1.1 |
| POE(54) castor oil | 0.8 |
| POE(30) sorbitan monotallate | 0.7 |
| Propyl gallate | 0.2 |
| 2-Ethylhexanol | 0.4 |
| Propylene glycol | 0.3 |
| AROMATIC 150 | balance |

Formulation H

| | % by weight |
|---|---|
| Clethodim Technical | 26.4 |
| C16-C18 fatty acid methyl esters | 30.4 |
| Ca DDBS | 1.3 |
| POE(54) castor oil | 1.0 |
| POE(30) sorbitan monotallate | 0.9 |
| Propyl gallate | 0.0 |
| 2-Ethylhexanol | 0.5 |
| Propylene glycol | 0.3 |
| AROMATIC 150 | balance |

Formulation I (example of formulation not according to the present invention)

| | % by weight |
|---|---|
| Clethodim Technical | 28.6 |
| C16-C18 fatty acid methyl esters | balance |
| TOXIMUL ® TAAS 5* | 1.8 |
| TRYLOX ® 5900** | 0.9 |
| TRYLOX ® 5907*** | 0.3 |
| Propyl gallate | 0.5 |

*ethoxylated tallow amine ether sulfate, available from Stepan Company
**POE(5) castor oil, HLB 4.9, available from Cognis Corporation
***POE(36) castor oil, HLB 12.6, available from Cognis Corporation

Example 1

The speed of herbicide absorption was compared. The results in Table I show that the various herbicidal formulations of the present invention result in more rapid herbicide absorption in ROUNDUP READY® corn, when compared to the commercial PRISM®1 EC formulation for clethodim.

Materials & Methods—General Application: ROUNDUP READY® corn was used in this example as the target weed species. Applications were made to actively growing corn which had reached 12-18 inches in height. All herbicide treatments were made using identical equipment and application methods.

Materials & Methods—Measuring Speed of Herbicide Absorption: The herbicide active ingredient in Formulation A (and related formulations B, C, D) and PRISM® is clethodim. It is known in public literature that clethodim acts in susceptible plants as a meristematic inhibitor. At the growth stage that these corn plants were treated, the meristematic region of the plant is imbedded inside the main stem tissue (in other words it is not exposed for direct chemical application). With the research methods used in this experiment the only known way the herbicide active ingredient could reach the meristem resulting in plant mortality is absorption through the leaf surface and subsequent translocation to the meristematic region.

In this example, all above ground leaf tissue was removed from the corn plants after treatment application (tissue was cut off and removed from the plant). This plant harvest technique occurred 30, 60 and 120 minutes after treatment application. Since absorption and translocation had to occur while the plant still had sprayed leaf tissue intact, plant control or plant mortality only occurred in those treatments whereby speed of absorption was complete within the time frame prior to plant harvest.

Results & Discussion: At 7 days after treatment (DAT) the treatments containing no added adjuvant (i.e., NIS, COC or AMS) had herbicide symptoms ranging from 0 to 93% control. Detailed data are contained in the following table:

TABLE I

| Product ID | Use Rate (lb ai/a) | % Control of RR Corn 7-DAT at 3 Different Plant Harvest Intervals. | | |
| --- | --- | --- | --- | --- |
| | | 30 minutes | 60 minutes | 120 minutes* |
| Untreated | — | 0 | 0 | 0 |
| Formulation A | 0.075 | 30 | 27 | 42 |
| Formulation B | 0.075 | 10 | 30 | 53 |
| Formulation C | 0.075 | 7 | 30 | 93 |
| Formulation D | 0.075 | 27 | 37 | 82 |
| Prism | 0.075 | 0 | 10 | 27 |

*At the 120 minute plant harvest interval all experimental clethodim formulations had numerically higher % RR corn control than did the commercial standard formulation Prism, indicating an increased speed of herbicide absorption as a function of these new experimental formulations. Formulation C had 93% control at the 120 minute plant harvest interval compared to 27% for Prism.

Significance: The enhanced clethodim formulations of the present invention are superior to PRISM® 1 EC due to increased speed of herbicide absorption, resulting in more rapid herbicide symptoms in susceptible weed species. The herbicide active ingredient clethodim is chemically unstable when exposed to UV radiation (i.e., intense sunlight). Therefore the longer the chemical resides on the outside of the leaf surface after application the more subject the herbicide is to degradation into non-herbicidal forms. A formulation that allows for quicker plant absorption will avoid this UV degradation problem and could possibly result in less active ingredient needed to control the undesired weed species.

Example 2

The speed of herbicide absorption was compared for herbicidal formulations with added ammonium sulfate. Ammonium sulfate is commonly used and often required as a tank mix adjuvant with glyphosate to increase efficacy. The results in Table II show that the herbicidal formulations of the present invention result in more rapid herbicide absorption in ROUNDUP READY® corn, when compared to PRISM® 1 EC, when ammonium sulfate is added to the herbicidal formulations.

Materials & Methods—General Application: ROUNDUP READY® corn was used in this example as the target weed species. Applications were made to actively growing corn which had reached 12-18 inches in height. All herbicide treatments included ammonium sulfate at 2.5 lbs per acre and were made using identical equipment and application methods.

Materials & Methods—Measuring Speed of Herbicide Absorption: The herbicide active ingredient in Formulation A (and related formulations B, C, D) and PRISM® is clethodim. It is known in public literature that clethodim acts in susceptible plants as a meristematic inhibitor. At the growth stage that these corn plants were treated, the meristematic region of the plant is imbedded inside the main stem tissue (in other words it is not exposed for direct chemical application). With the research methods used in this experiment the only known way the herbicide active ingredient could reach the meristem resulting in plant mortality is absorption through the leaf surface and subsequent translocation to the meristematic region.

In this example, all above ground leaf tissue was removed from the corn plants after treatment application (tissue was cut off and removed from the plant). This plant harvest technique occurred 30, 60 and 120 minutes after treatment application. Since absorption and translocation had to occur while the plant still had sprayed leaf tissue intact, plant control or plant mortality only occurred in those treatments whereby speed of absorption was complete within the time frame prior to plant harvest.

Results & Discussion: At 7 days after treatment (DAT) the treatments containing ammonium sulfate as an added adjuvant had herbicide symptoms ranging from 0 to 97% control. Detailed data are contained in the following table:

TABLE II

| Product ID** | Use Rate (lb ai/a) | % Control of RR Corn 7-DAT at 3 Different Plant Harvest Intervals. | | |
| --- | --- | --- | --- | --- |
| | | 30 minutes | 60 minutes | 120 minutes* |
| Untreated | — | 0 | 0 | 0 |
| Formulation A | 0.075 | 7 | 43 | 93 |
| Formulation B | 0.075 | 17 | 13 | 85 |
| Formulation C | 0.075 | 0 | 94 | 97 |
| Formulation D | 0.075 | 0 | 60 | 97 |
| Prism | 0.075 | 30 | 28 | 37 |

*At the 120 minute plant harvest interval all experimental clethodim formulations had numerically higher % RR corn control than did the commercial standard formulation Prism, indicating an increased speed of herbicide absorption as a function of these new experimental formulations. Formulations C and D had 97% control at the 120 minute plant harvest interval compared to 37% for Prism. At the 60 minute plant harvest interval Formulation C had 94% control.
**All treatments had ammonium sulfate added at 2.5 lbs product/acre.

Significance: The results of Example 1 demonstrate that the enhanced clethodim formulations of the present invention are superior to PRISM® 1 EC, due to increased speed of herbicide absorption, resulting in more rapid herbicide symptoms in susceptible weed species. This Example shows that the formulations of the present invention also demonstrate increased speed of herbicide absorption when mixed with ammonium sulfate.

Example 3

Formulations A and E of the present invention were compared with SELECT® 2 EC in their ability to control volunteer ROUNDUP READY® corn when tank mixed with glyphosate without the addition of a crop oil concentrate (COC) adjuvant. The results in Tables IIIA and IIIB show that the formulations of the present invention provide superior control under these conditions.

Materials & Methods—General Application: ROUNDUP READY® soybeans were used in these examples with ROUNDUP READY® volunteer corn as the target grass species. Application was made to actively growing soybeans and ROUNDUP READY® volunteer corn. All herbicide treatments, within a test, were made using identical equipment and application methods.

Results & Discussion: At 1 month after application, the treatments containing Formulations A and E, without the addition of any COC adjuvant, resulted in more complete control compared to Select 2 EC. Detailed data are contained in the following tables:

TABLE IIIA

| Location | Corn Size | Product ID Use Rate (lb ai/a) glyphosate + clethodim DAT | Untreated | Glyphosate + Formulation A* 0.75 to 1.0 + 0.063 % Control | Glyphosate + Select* 0.75 to 1.0 + 0.063 |
|---|---|---|---|---|---|
| Purdue University | — | — | 0 | 95 | 73 |
| Kansas State University | 10 to 16" | 30 | 0 | 99 | 48 |
| Alvey Ag Research | 10 to 12" | 29 | 0 | 97 | 53 |
| Van Diest, Harlan, IA | 24 to 28" | 37 | 0 | 88 | 48 |
| University of Illinois | 18 to 24" | 12 | 0 | 93 | 73 |
| Ohio State University | 9 to 10" | 29 | 0 | 90 | 65 |
| Greenville, MS | 12 to 14" | 34 | 0 | 92 | 84 |
| Average | — | — | 0.0 | 94.4 | 63.4 |

*All treatments had ammonium sulfate added at 2.5 lbs product/acre.

TABLE IIIB

| Location | Corn Size | Product ID Use Rate (lb ai/a) glyphosate + clethodim DAT | Untreated | Glyphosate + Formulation E 0.78 + 0.088 % Control | Glyphosate + Select 0.78 + 0.094 |
|---|---|---|---|---|---|
| Greenville, MS | 18 to 25" | 23 | 0 | 86 | 15 |

Significance: Clethodim is known to provide excellent control of a wide array of grassy weeds; however, the effectiveness of clethodim is dependent on the addition of a COC adjuvant, which may not always be a desirable addition to the spray program, and is in fact prohibited on many glyphosate labels. The enhanced clethodim formulations of the present invention provide more complete control of grasses than SELECT®2 EC in glyphosate tank mixes without the addition of a COC adjuvant.

Example 4

The control of ROUNDUP READY® corn at 7 and 14 days after treatment (DAT) was compared for the herbicidal formulations of the present invention and PRISM® 1 EC. The results presented in Table IV show that the formulations of the present invention demonstrate increased speed of control, resulting in more rapid herbicide symptoms in susceptible weed species.

Materials & Methods—General Application: ROUNDUP READY® corn was used in this example as the target weed species. Applications were made to actively growing corn which had reached 12-18 inches in height. All herbicide treatments were made using identical equipment and application methods.

Results & Discussion: At 7 and 14 days after treatment (DAT) the treatments containing Formulations A, B, C, and D resulted in quicker and more complete grass control compared to the commercial PRISM® formulation. Detailed data are contained in the following table:

TABLE IV

| | Use Rate | % Control of RR Corn at 7 and 14 Days After Treatment | |
|---|---|---|---|
| Product ID | (lb ai/a) | 7 DAT | 14 DAT |
| Untreated | — | 0 | 0 |
| Formulation A | 0.075 | 51.7 | 91.7 |
| Formulation B | 0.075 | 41.7 | 90.0 |
| Formulation C | 0.075 | 70.0 | 97.7 |
| Formulation D | 0.075 | 55.0 | 97.0 |
| Prism | 0.075 | 36.7 | 85.0 |

Significance: Clethodim is known to provide excellent control of a wide array of grassy weeds, however the speed of visual activity generally requires up to 10 days. The clethodim formulations of the present invention provide much quicker visual control symptoms than PRISM®, providing the user with an earlier assurance that the product is working.

Example 5

The control of ROUNDUP READY® corn at 7 and 14 days after treatment (DAT) was compared for the herbicidal formulations of the present invention and PRISM® 1 EC, where ammonium sulfate was added to the formulations. Ammonium sulfate is commonly used and often required as a tank mix adjuvant with glyphosate to increase efficacy. The results presented in Table V show that the formulations of the present invention demonstrate increased speed of control under these conditions.

Materials & Methods—General Application: ROUNDUP READY® corn was used in this example as the target weed species. Applications were made to actively growing corn which had reached 12-18 inches in height. All herbicide treatments included ammonium sulfate at 2.5 lbs per acre and were made using identical equipment and application methods.

Results & Discussion: At 7 and 14 days after treatment (DAT) the treatments containing Formulations A, B, C, and D resulted in quicker and more complete grass control compared to the commercial PRISM® formulation of clethodim. Detailed data are contained in the following table:

TABLE V

| Product ID* | Use Rate (lb ai/a) | % Control of RR Corn at 7 and 14 Days After Treatment | |
|---|---|---|---|
| | | 7 DAT | 14 DAT |
| Untreated | — | 0 | 0 |
| Formulation A | 0.075 | 55.0 | 96.0 |
| Formulation B | 0.075 | 51.7 | 96.0 |
| Formulation C | 0.075 | 85.0 | 98.3 |
| Formulation D | 0.075 | 88.3 | 99.3 |
| Prism | 0.075 | 41.7 | 91.7 |

*All treatments had ammonium sulfate added at 2.5 lbs product/acre.

Significance: Clethodim is known to provide excellent control of a wide array of grassy weeds, however the speed of visual activity generally requires up to 10 days. The clethodim formulations of the present invention, with added ammonium sulfate, provide much quicker visual control symptoms than PRISM®, providing the user with an earlier assurance that the product is working.

Example 6

Select 2 EC tank mixed with a nonionic surfactant (NIS) adjuvant and Formulation A of the present invention were compared for their ability to increase the speed of glyphosate absorption in several weed species. The results in Table VI show that the tank mix of glyphosate with Formulation A increased the speed of glyphosate absorption compared to both glyphosate alone and glyphosate tank mixed with SELECT® plus a NIS adjuvant, resulting in more rapid herbicide symptoms in susceptible weed species.

Materials & Methods—General Application: ROUNDUP READY® soybeans were used in this example as the crop, and indigenous common lambsquarters (*Chenopodium album*) and giant foxtail (*Setaria faben*), as well as sowed ROUNDUP READY® corn, were used as target weed species. The source of the glyphosate was ROUNDUP WEATHERMAX®, a product of Monsanto. A single application was made to actively growing weeds, which had reached 1 to 13 inches in height. All herbicide treatments included ammonium sulfate at 2.5 lbs per acre and were made using identical equipment and application methods.

Results & Discussion: At 8 and 14 days after treatment (DAT) the treatments containing SELECT® 2 EC plus NIS adjuvant and Formulation A, which have no biological activity on broadleaf plants such as common lambsquarters, both resulted in quicker and in some cases more complete weed control compare~ to the glyphosate treatment applied alone. But the Formulation A treatment was even better than the SELECT® 2 EC treatment which contained an added tank mix adjuvant (NIS). Detailed data are contained in the following table:

Significance: Glyphosate is known for providing slow and effective control of problem weeds. Efforts to increase the speed of control have historically resulted in a decrease in overall control at >14 days after treatment (DAT), although the control at <14 DAT may have been have been increased. The addition of Formulation A to the glyphosate treatment, which was intended to control volunteer ROUNDUP READY® corn, not only controlled the ROUNDUP READY® corn, but also increased the speed of common lambsquarters and giant foxtail control (8 DAT rating) without decreasing the overall control at 14 DAT compared to glyphosate alone and glyphosate plus SELECT® 2 EC.

Example 7

Table VII illustrates that the clethodim formulations of the present invention are superior to SELECT® 2 EC, even when used at a lower amount of active ingredient per acre, because they can be tank-mixed with other herbicides without a decrease in grass control.

Materials & Methods—General Application: Peanuts were used in this example with Texas panicum (*Panicum texanum*) as the target weed species. The additional herbicides used were CADRE® (active ingredient imazapic, available from BASF Corporation), STORM™ (active ingredients acifluorfen and bentazone, available from United Phosphorus Incorporated), and COBRA® (active ingredient lactofen, available from Valent U.S.A. Corporation). Applications were made to actively growing panicum which had reached 6 inches in height. All herbicide treatments were made using identical equipment and application methods.

Results & Discussion: At 53 days after treatment, the treatments containing Formulation B resulted in no antagonism and superior control when tank-mixed with common broadleaf peanut herbicides that are known to be antagonistic to clethodim's postemergence grass activity. Formulation B applied at 80% of the dose rate of SELECT® and tank-mixed with common broadleaf herbicides resulted in weed control superior to SELECT® when tank-mixed with STORM™ and COBRA®, and equal weed control when tank-mixed with CADRE®. Detailed data are contained in the following table:

TABLE VII

| Product ID* | Use Rate (ounces of product/acre) | % Control of Texas Panicum at 53 Days After Treatment | |
|---|---|---|---|
| | | Select @ 0.125 lb ai/a | Formulation B @ 0.10 lb ai/a |
| — | — | 98.0 | 92.3 |
| Cadre | 1.44 | 95.8 | 94.5 |
| Storm | 24 | 81.3 | 93.3 |
| Cobra | 12.5 | 83.8 | 91.0 |

*All treatments contained COC.

TABLE VI

| Product ID* | Use Rate (lb ai/a) | % Weed Control at 8 and 14 DAT | | | | | |
|---|---|---|---|---|---|---|---|
| | | common lambsquarters | | giant foxtail | | RR volunteer corn | |
| | | 8 DAT | 14 DAT | 8 DAT | 14 DAT | 8 DAT | 14 DAT |
| Untreated | — | 0 | 0 | 0 | 0 | 0 | 0 |
| Roundup WeatherMax | 1.00 | 91.7 | 93.3 | 91.7 | 97.7 | 0 | 0 |
| Roundup WeatherMax + Formulation A | 1.00 + 0.078 | 97.7 | 97.7 | 99.0 | 96.3 | 73.3 | 81.8 |
| Roundup WeatherMax + Select + NIS | 1.0 + 0.078 + 0.25% v/v | 96.3 | 96.3 | 97.6 | 99.9 | 68.3 | 81.6 |

*All treatments had ammonium sulfate added at 2.5 lbs product/acre.

Significance: Clethodim is known to provide excellent control of a wide array of grassy weeds; however, some commonly used postemergence broadleaf herbicides are known to reduce clethodim's grass activity (antagonism) when tank-mixed with clethodim. The clethodim formulations of the present invention can be tank-mixed with these broadleaf herbicides without a decrease in grass control, even when used at a lower amount of active ingredient per acre than the commercial SELECT® 2 EC formulation.

Example 8

Table VIII illustrates that the enhanced clethodim formulations of the present invention are superior to SELECT® 2 EC, because they do not require a crop oil concentrate (COC) adjuvant to provide commercially acceptable grass control, unlike current commercial clethodim formulations.

Materials & Methods—General Application: ROUNDUP READY® cotton was used in this example with barnyardgrass (*Echinochloa crus galli*) as the target grass species. Application was made to actively growing cotton and barnyardgrass which had reached 6-10 inches in height. All herbicide treatments included ammonium sulfate at 2.5 lbs per acre and were made using identical equipment and application methods.

Results & Discussion: At 7 and 33 days after treatment (DAT) the treatments containing Formulations A and B without the addition of a COC adjuvant resulted in quicker and more complete grass control compared to the commercial SELECT® 2 E~formulation. Detailed data are contained in the following table:

TABLE VIII

| | | % Control of Barnyardgrass at 7 and 33 Days After Treatment | | | |
| | Use Rate | 7 DAT | | 33 DAT | |
| Product ID* | (lb ai/a) | −COC | +COC | −COC | +COC |
|---|---|---|---|---|---|
| Untreated | — | 0 | 0 | 0 | 0 |
| Formulation A | 0.094 | 73.3 | 70.0 | 96.0 | 96.7 |
| Formulation B | 0.094 | 70.0 | 73.3 | 97.0 | 97.7 |
| Select 2 EC | 0.094 | 41.7 | 70.0 | 46.7 | 84.0 |

*All treatments had ammonium sulfate added at 2.5 lbs product/acre.

Significance of Invention: Clethodim is known to provide excellent control of a wide array of grassy weeds. However, the effectiveness of clethodim has thus far been dependent on the addition of a COC adjuvant, which may not always be a desirable addition to the spray program. The enhanced clethodim formulations of the present invention provide faster and more complete control without the addition of a COC.

Example 9

Several formulations of the present invention were tested for chemical stability along with a comparative clethodim formulation containing C16-C18 fatty acid methyl esters. Table IX illustrates that the enhanced clethodim formulations of the present invention are storage stable for extended periods and have improved chemical stability compared to a similar formulation not of the present invention.

Materials and Methods: Several formulations were tested for stability of the active ingredient over various time periods at 40° C. or at room temperature. The percent clethodim remaining was calculated based on a starting clethodim value of 100%.

Results and Discussion: The chemical stability results are indicated in the following Table IX. The chemical stability of formulations containing clethodim is an important consideration, since many standard adjuvant materials and surfactants, including calcium DDBS, are known in the art to cause rapid degradation of clethodim and other cyclohexanedione oximes. Yet the results show that these formulations are unexpectedly stable over extended periods of time.

TABLE IX

| | Storage | % Clethodim Remaining Storage Time | | |
| Product ID | Temperature. | 2 months | 6 months | 12 months |
|---|---|---|---|---|
| Formulation A | 40° C. | 95.9 | — | — |
| | room temp. | — | 97.5 | — |
| Formulation B | 40° C. | 95.4 | — | — |
| | room temp. | — | 98.0 | — |
| Formulation C | room temp. | — | 93.6 | — |
| Formulation D | room temp. | — | 93.9 | — |
| Formulation F | 40° C. | 92.9 | — | — |
| | room temp. | — | 98.4 | 95.2 |
| Formulation G | 40° C. | 92.9 | — | — |
| | room temp. | — | 97.5 | 94.0 |
| Formulation H | 40° C. | 91.7 | — | — |
| | room temp. | — | 99.6 | 93.2 |
| Formulation I* | room temp. | — | 87.9 | — |

*Formulation I was tested for comparison purposes and is not a formulation of the present invention.

Significance: Addition of many types of adjuvant materials and surfactants, including calcium DDBS, to formulations of clethodim and other cyclohexanedione oximes can cause rapid degradation of the active ingredient. The formulations of the present invention contain significant amounts of a fatty acid methyl ester adjuvant and calcium DDBS and yet are chemically stable over extended periods of time. They also show improved chemical stability over a formulation not of the present invention which also contains a fatty acid methyl ester adjuvant.

The invention claimed is:

1. An herbicidal composition comprising:
    (a) an effective amount of an herbicidal cyclohexanedione oxime compound or agriculturally acceptable salt thereof;
    (b) one or more esters of a fatty acid;
    (c) a salt of dodecylbenzenesulfonic acid; and
    (d) at least one nonionic surfactant selected from the group consisting of polyoxyethylene plant oils and polyoxyethylene sorbitan esters wherein the nonionic surfactant has a hydrophilic-lipophilic balance (HLB) value of about 14.4-18.0;
with the proviso that the composition does not include additional phenylpyrazole safeners.

2. The herbicidal composition of claim 1 wherein said herbicidal cyclohexanedione oxime compound is clethodim, sethoxydim, alloxydim, cycloxydim, butroxydim, tralkoxydim, tepraloxydim, or profoxydim.

3. The herbicidal composition of claim 1 wherein said herbicidal cyclohexanedione oxime compound is clethodim or sethoxydim.

4. The herbicidal composition of claim 1 wherein said herbicidal cyclohexanedione oxime compound is clethodim.

5. The herbicidal composition of claim 1 that contains 3 to 30% by weight of said herbicidal cyclohexanedione oxime compound or agriculturally acceptable salt thereof.

6. The herbicidal composition of claim 1 wherein said esters of a fatty acid are C1-C8 alkyl esters of C12-C22 organic monobasic acids.

7. The herbicidal composition of claim 1 wherein said esters of a fatty acid are methyl oleate, methyl palmitate, isopropyl myristate, octyl laurate, isopropyl palmitate, butyl stearate, or mixtures thereof.

8. The herbicidal composition of claim 1 that contains 0.5 to 8% of said nonionic surfactant.

9. The herbicidal composition of claim 1 that contains 0.5 to 5% of said salt of dodecylbenzenesulfonic acid.

10. An herbicidal composition of claim 1 that includes at least one additional herbicide.

11. An herbicidal composition of claim 10 where the at least one additional herbicide is selected from glyphosate, lactofen, imazapic, acifluorfen, bentazone and/or pyrithiobac-sodium.

12. An herbicidal composition of claim 11 where the additional herbicide is glyphosate.

13. An herbicidal composition of claim 11 where the additional herbicide is lactofen.

14. An herbicidal composition of claim 11 where the additional herbicide is imazapic.

15. An herbicidal composition of claim 11 where the additional herbicide is acifluorfen.

16. An herbicidal composition of claim 11 where the additional herbicide is bentazone.

17. An herbicidal composition of claim 11 where the additional herbicide is pyrithiobac-sodium.

18. The herbicidal composition of claim 1 or 10 that comprises one or more additional solvents.

19. The herbicidal composition of claim 18 wherein said additional solvents are selected from the group consisting of 2-ethylhexanol, propylene glycol, ethylene glycol, diethylene glycol, and glycerin.

* * * * *